United States Patent [19]

White et al.

[11] Patent Number: 4,626,522
[45] Date of Patent: Dec. 2, 1986

[54] BENZOXAZOCINES INTERMEDIATES

[75] Inventors: Alan C. White, Windsor; Robin G. Shepherd, Burnham, both of England

[73] Assignee: John Wyeth & Brother Limited, Maidenhead, England

[21] Appl. No.: 303,436

[22] Filed: Sep. 18, 1981

Related U.S. Application Data

[62] Division of Ser. No. 214,078, Dec. 8, 1980, Pat. No. 4,318,909.

[51] Int. Cl.⁴ .............................................. C07C 93/08
[52] U.S. Cl. ................................... 564/355; 564/220; 564/338; 564/339; 558/422
[58] Field of Search ............... 564/355, 220, 338, 339; 260/465 F

[56] References Cited

U.S. PATENT DOCUMENTS

| | | | |
|---|---|---|---|
| 3,151,124 | 9/1964 | Huebner | 564/355 X |
| 3,393,192 | 7/1968 | Walter et al. | 564/355 X |
| 3,441,564 | 4/1969 | Krapcho | 260/333 X |
| 3,459,803 | 8/1969 | Faust et al. | 564/355 |
| 3,794,639 | 2/1974 | Krapcho et al. | 260/333 X |
| 3,830,303 | 8/1974 | Klous et al. | 260/333 X |
| 3,978,085 | 8/1976 | Eberlin | 260/333 |
| 4,100,277 | 7/1978 | Demerson | 260/333 X |
| 4,125,538 | 11/1978 | Standridge | 260/333 X |

OTHER PUBLICATIONS

Mentrup et al., "Chemical Abstracts", vol. 27, Section No. 139605, (1973).
Basil et al., J. Med. Chem. (1970), 13, pp. 403-406.
C.A. 69 (1968), 27400r, Dall'Oata et al.
C.A., 77 (1972) 147550c, Caputi et al.
C.A., 78 (1978), 147929d, Oryales et al.
C.A., 80 (1980), 829824t, Kawamoto et al.
C.A., 84 (1984), 4193u, Badilercer et al.

Primary Examiner—Robert V. Hines
Attorney, Agent, or Firm—Richard K. Jackson

[57] ABSTRACT

Novel benzoxazocines of formula (I)

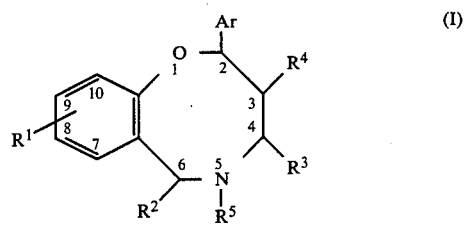

and their pharmaceutically acceptable acid addition salts, wherein $R^1$ represents hydrogen, or one or more halogen, trifluoromethyl, lower alkyl, lower alkoxy, nitro, amino acylamino, mono- or di- (lower)alkylamino or cyano substituents, $R^2$, $R^3$ and $R^4$, which may be the same or different, each represent hydrogen or lower alkyl or $R^3$ and $R^4$ together represent —(CH$_2$)$_3$— or —(CH$_2$)$_4$—, $R^5$ represents hydrogen, lower alkyl, phenyl(lower)alkyl or cycloalkyl(lower)alkyl, and Ar is a phenyl radical optionally substituted by one or more halogen, trifluoromethyl, lower alkyl, lower alkoxy, nitro or amino groups exhibit activity on the central nervous system, particularly as antidepressants. The compounds can be prepared from novel alcohols of formula (II)

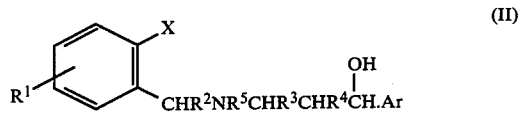

wherein $R^1$, $R^2$, $R^3$, $R^4$, $R^5$ and Ar are as defined above and X is fluorine, chlorine or bromine.

5 Claims, No Drawings

BENZOXAZOCINES INTERMEDIATES

This is a division of application Ser. No. 214,078, filed Dec. 8, 1980, and now U.S. Pat. No. 4,318,909.

This invention relates to benzoxazocines, to pharmaceutical compositions containing them, to the use of the benzoxazocines, to processes for preparing them and to novel intermediates useful in the said processes.

The present invention provides novel benzoxazocines of the general formula (I)

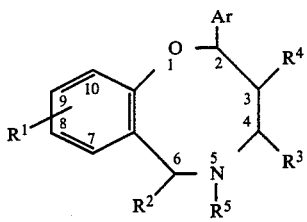

and their pharmaceutically acceptable acid addition salts, wherein $R^1$ represents hydrogen, or one or more halogen, trifluoromethyl, lower alkyl, lower alkoxy, nitro, amino, acylamino, mono- or di-(lower)alkylamino or cyano substituents, $R^2$, $R^3$ and $R^4$, which may be the same or different, each represent hydrogen or lower alkyl or $R^3$ and $R^4$ together represent —$(CH_2)_3$— or —$(CH_2)_4$—, $R^5$ represents hydrogen, lower alkyl, phenyl(lower)alkyl or cycloalkyl(lower)alkyl, and Ar is a phenyl radical optionally substituted by one or more halogen, trifluoromethyl, lower alkyl, lower alkoxy, nitro or amino groups.

The term "lower" as used herein means that the radical referred to contains 1 to 6 carbon atoms. The radical preferably contains 1 to 4 carbon atoms. For example when one or more of the groups $R^2$, $R^3$, $R^4$ and $R^5$ is lower alkyl, the group may be, for example, methyl, ethyl, propyl, or butyl. When $R^5$ is cycloalkyl(lower)alkyl, the lower alkyl group is preferably methyl; preferred cycloalkyl(lower)alkyl groups are cyclobutylmethyl and cyclopropylmethyl. Examples of phenyl(lower)alkyl groups include benzyl and phenethyl.

Preferably $R^2$, $R^3$ and $R^4$ are all hydrogen and $R^5$ is lower alkyl. Preferred meanings for $R^1$ are hydrogen, nitro and trifluoromethyl (particularly in the 8-position of the benzoxazocine ring). Ar is preferably an unsubstituted phenyl radical or a phenyl radical substituted by one or two of the substituents mentioned hereinabove (particularly halogen or lower alkyl). A particularly preferred compound of the invention is 5-methyl-2-phenyl-2,3,4,5-tetrahydro-[64]-1,5-benzoxazocine or a pharmaceutically acceptable acid addition salt thereof.

The compounds of the invention can be prepared by cyclodehydrohalogenating an alcohol of general formula (II)

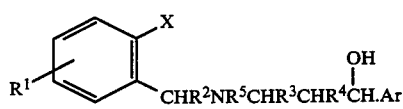

wherein $R^1$, $R^2$, $R^3$, $R^4$, $R^5$ and Ar are as defined above and X is fluorine, chlorine or bromine. The cyclodehydrohalogenation can be carried out by reacting the alcohol with a strong base such as potassium or sodium hydride or lithium diisopropylamide in a dipolar aprotic solvent. The strong base is preferably sodium hydride. Examples of dipolar aprotic solvents include dimethylsulphoxide, dimethylformamide, hexamethylphosphoric triamide and sulpholane. Preferably the concentration of the alcohol in the solvent is relatively low so as to encourage intramolecular cyclisation. The halogen substituent X in the alcohol is preferably fluorine but the choice of suitable halogen can depend upon the substituent $R^1$; if $R^1$ is an activating substituent such as nitro or cyano then X can be fluorine, chlorine or bromine while if $R^1$ is hydrogen or a less activating substituent such as trifluoromethyl, lower alkyl or halogen then X should be fluorine.

Once a benzoxazocine of general formula (I) is obtained it may be converted into another benzoxazocine of general formula (I) by methods known in the art.

For example a benzoxazocine of formula (I) in which $R^1$ is chlorine, bromine or iodine can be converted to the lithium derivative by treatment with e.g. an alkyl lithium and then to a nitrile, by treatment with cyanogen chloride or to a nitro or nitroso group by the methods of Corey and Estreicher, Tet. Letters 1980, 21, 1113 and Bartlett et al J.Chem Soc., (C) 1970, 1717. The nitroso group can be subsequently oxidised to a nitro group.

The nitro derivatives may be reduced to the amino derivatives which may be acetylated to the acetamino derivatives. Compounds in which $R^1$ is amino may be diazotised and the diazonium salt converted by known procedures to compounds in which $R^1$ is halogen, hydroxy, alkoxy or nitrile. A benzoxazocine of formula (I) in which $R^5$ is hydrogen may be alkylated to a compound in which $R^5$ is lower alkyl, phenyl(lower)alkyl or cycloalkyl(lower)alkyl by treatment with an alkylating agent, e.g. a lower alkylphenyl(lower)alkyl- or cycloalkyl(lower)alkyl-halide in presence of an acid acceptor. Alternatively the compound of general formula (I) in which $R^5$ is hydrogen may be alkylated by reductive alkylation, i.e. by treatment with an aldehyde and hydrogen in presence of a hydrogenation catalyst. A preferred method of cycloalkyl-methylating involves reacting the N-unsubstituted compound with a cycloalkylcarbonyl chloride to give an intermediate N-carbonyl cycloalkyl compound which may be reduced with, for example, a hydride transfer agent.

If in any of the processes described above the compound of the general formula (I) is obtained as an acid addition salt, such as a pharmaceutically acceptable acid addition salt, the free base can be obtained by basifying a solution of the acid addition salt. Conversely, if the product of the process is a free base a pharmaceutically acceptable acid addition salt may be obtained by dissolving the free base in a suitable organic solvent and treating the solution with an acid, in accordance with the conventional procedures for preparing acid addition salts from base compounds.

Examples of acid addition salts are those formed from inorganic and organic acids, such as sulphuric, hydrochloric, hydrobromic, phosphoric, tartaric, fumaric, maleic, citric, acetic, formic, methanesulphonic and p-toluenesulphonic acids.

The compounds of general formula (I) possess one or more asymmetric carbon atoms, depending upon the particular substituents. The compounds can therefore exist in various stereochemical forms. It will be realised that if the starting material of formula (II) is a mixture of isomers the product of formula (I) will also be a mixture of isomers which may be separated, if required, by standard procedures. If the starting material is a single isomer then the product will also be a single isomer.

The alcohols of general formula (II) and their acid addition salts are novel compounds and are also provided by this invention. These compounds may be prepared by reacting a halo compound of general formula (III)

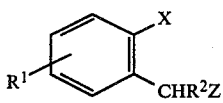

where $R^1$, $R^2$ and X are as defined above and Z is an amino group of formula $NHR^5$ where $R^5$ is as defined above or a leaving group such as a halogen atom or a tosylate radical, with an alcohol of general formula (IV)

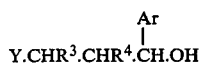

where Ar, $R^3$ and $R^4$ are as defined above and Y is an amino group of formula $NHR^5$ where $R^5$ is as defined above or a leaving group such as a halogen atom or a tosylate radical with the proviso that one of Y and Z is an amino group of formula $NHR^5$ and the other is a leaving group. Preferably Z is the leaving group (preferably a halogen atom, e.g. chlorine) and Y is an amino group $NHR^5$. The starting materials of formulae (III) and (IV) are known compounds or can be prepared in an analogous manner to that used for known compounds. For example, the benzyl halides of general formula (III) can be prepared from corresponding benzyl alcohols.

The compounds of general formula (I) and their pharmaceutically acceptable acid addition salts possess pharmacological acitivity. In particular the compounds exhibit activity on the central nervous system, e.g. as antidepressants, as indicated by standard pharmacological test procedures. One procedure measures the inhibition of p-chloroamphetamine induced hyperactivity in mice. This procedure detects 5-hydroxytryptamine uptake inhibitors which are potential antidepressant agents. The procedure involves administering the test compounds to three groups of 4 female mice and a requisite volume of vehicle to a fourth control group. Thirty minutes later all the animals are given 20 mg/kg p-chloroamphetamine i.p. The grouped mice are placed immediately in cages in activity monitors and their motor activity recorded over the period 10 to 30 minutes after p-chloramphetamine administration. When tested by this procedure 5-methyl-2-phenyl-2,3,4,5-tetrahydro-[6H]-1,5-benzoxazocine, a representative compound of the invention, shows marked inhibition of the p-chloramphetamine induced hyperactivity. The $ED_{50}$ of the tosylate was found to be 11 mg/kg p.o.

Some of the compounds of the invention (for example, 2-phenyl-2,3,4,5-tetrahydro-[6H]-1,5-benzoxazocine and 5-ethyl-2-phenyl-2,3,4,5-tetrahydro-[6H]-1,5-benzoxazocine) also possess analgesic activity as indicated by their activity in standard pharmacological procedures.

The invention further provides a method of treating depression which comprises administering to an animal, particularly a human, a therapeutically effective amount of a compound of the invention. The invention also provides a compound of the invention for use as an antidepressant agent. Also provided is a pharmaceutical composition comprising a compound of the invention in association with a pharmaceutically acceptable carrier. Any suitable carrier known in the art can be used to prepare the pharaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is with it. Similarly cachets are included.

Sterile liquid form compositions include sterile solutions, suspensions, emulsions, syrups and elixirs. The active ingredients can be dissolved or suspended in a pharmaceutically acceptable sterile liquid carrier, such as sterile water, sterile organic solvent or a mixture of both. Preferably a liquid carrier is one suitable for parenteral injection. Where the active ingredient is sufficiently soluble it can be dissolved in normal saline as a carrier; if it is too insoluble for this it can often be dissolved in a suitable organic solvent, for instance aqueous propylene glycol or polyethylene glycol solutions. Aqueous propylene glycol containing from 10 to 75% of the glycol by weight is generally suitable. In other instances other compositions can be made by dispersing the finely-divided active ingredient in aqueous starch or sodium carboxymethyl cellulose solution, or in a suitable oil, for instance arachis oil. Liquid pharmaceutical compositions which are sterile solutions or suspensions can be utilised by intramuscular, intraperitoneal or subcutaneous injection. In many instances a compound is orally active and can be administered orally either in liquid or solid composition form.

Preferbly the pharmaceutical composition is in unit dosage form, e.g. as tablets or capsules. In such form, the composition is sub-divided in unit doses containing appropriate quantities of the active ingredient; the unit dosage forms can be packaged compositions, for example packeted powders or vials or ampoules. The unit dosage form can be a capsule, cachet or tablet itself, or it can be the appropriate number of any of these in package form. The quantity of the active ingredient in a unit dose of composition may be varied or adjusted from 5 mg. or less to 500 mg. or more, according to the particular need and the activity of the active ingredient.

The following Examples illustrate the invention:

EXAMPLE 1

N-(2-Fluorophenylmethyl)-3-hydroxy-3-phenylpropylamine

A mixture of 3-hydroxy-3-phenylpropylamine (7.0 g, 46 mM) and 2,2,6,6-tetramethylpiperidine (7.9 ml, 46 mM) in acetonitrile (100 ml) was treated with a solution of o-fluorobenzyl chloride (6.75 g, 46 mM) in acetonitrile (10 ml). After 24 hours the resulting precipitate was removed by filtration and washed with acetonitrile (2×10 ml). The combined filtrate and washings were evaporated under reduced pressure and the residue partitioned between 2N hydrochloric acid (50 ml) and ether (100 ml). The aqueous layer was basified and extracted with ether, the ether extracts dried and evaporated. Chromatography on Grade 3 silica using 2% methanol in chloroform as eluant followed by distillation gave the title compound (6.3 g) b.p. 156°–160° C. (0.2 mbar).

Found: C, 73.9; H, 7.1; N, 5.2% $C_{16}H_{18}FNO$ requires: C, 74.1; H, 7.0; N, 5.4%.

EXAMPLE 2

2-Phenyl-2,3,4,5-tetrahydro-[6H]-1,5-benzoxazocine

A mixture of N-(2-fluorophenylmethyl)-3-hydroxy-3-phenylpropylamine (4.5 g, 17 mM), 50% sodium hydride dispersion (870 mg, 17 mM) and dimethylsulphoxide (200 ml) was stirred for 24 hours at 50° C. under argon. The mixture was cooled to ambient temperature, poured onto water (700 ml) and extracted with ether (3×200 ml). The combined ether layers were extracted with 1N hydrochloric acid (3×50 ml), the acid layer basified and extracted with ether (2×200 ml). The organic phase was dried and the solvent removed under reduced pressure. Recrystallisation from cyclohexane gave the title compound (1.7 g) m.p. 73°–4° C.

Found: C, 80.1; H, 7.4; N, 5.9% $C_{16}H_{17}NO$ requires: C, 80.3; H, 7.2; N, 5.9%.

EXAMPLE 3

N-(2-Fluorophenylmethyl)-3-hydroxy-N-methyl-3-phenylpropylamine

A mixture of 3-hydroxy-N-methyl-3-phenylpropylamine (8.3 g, 50 mM), 2,2,6,6-tetramethylpiperidine (8.4 ml, 50 mM), o-fluorobenzyl chloride (7.25 g, 50 mM) and acetonitrile (100 ml) was stirred for 24 hours at ambient temperature. The resulting precipitate was removed by filtration, the precipitate washed with acetonitrile and the combined filtrate and washings evaporated under reduced pressure. The residue was partitioned between 2N hydrochloric acid (100 ml) and ether (100 ml), the aqueous layer basified and extracted with ether (2×100 ml). The ether extract was dried and the solvent removed under reduced pressure to yield an oil (10.3 g). Distillation gave the title compound b.p. 160°–2° C./0.6 mbar.

Found: C, 74.4; H, 7.3; N, 5.4% $C_{17}H_{20}FNO$ requires: C, 74.7; H, 7.4; N, 5.1%.

EXAMPLE 4

5-Methyl-2-phenyl-2,3,4,5-tetrahydro-[6H]-1,5-benzoxazocine

A mixture of N-(2-fluorophenylmethyl)-3-hydroxy-N-methyl-3-phenylpropylamine (6.0 g,), 50% sodium hydride dispersion (1.1 g) and dimethyl sulphoxide (100 ml) was maintained for 24 hours at 50° C. under argon. The mixture was poured onto water (500 ml) and extracted with ether (2×500 ml). The ether was dried and the solvent removed under reduced pressure. The residue was chromatographed on Grade 3 silica (250 g) using 2% methanol in chloroform as eluant. Evaporation of the appropriate fractions, dissolution of the residue in ether and treatment with an excess of tosic acid in ether gave a crystalline precipitate. Recrystallisation from isopropyl alcohol gave the title compound as the tosylate (3.4 g) m.p. 188°–9° C.

Found: C, 67.7; H, 6.2; N, 3.15% $C_{17}H_{19}NO.C_7H_8SO_3$ requires: C, 67.7; H, 6.4; N, 3.3%.

EXAMPLE 5

3-(4-Chlorophenyl)-N-(2-fluorophenyl)methyl-3-hydroxy-N-methylpropylamine

A mixture of 3-(4-chlorophenyl)-3-hydroxy-N-methylpropylamine (prepared by borane-THF reduction of β-p-dichloropropiophenone followed by reaction of the resulting chloro-alcohol with methylamine in ethanol) (10 g, 50 mmM), 2,2,6,6-tetramethylpiperidine (8.4 ml, 50 mM), o-fluorobenzyl chloride (7.25 g, 50 mM) and acetonitrile (100 ml) was stirred for 24 hours at ambient temperature. The mixture was filtered, the filtrate evaporated and the residue partitioned between 2N hydrochloric acid and ether. The aqueous layer was basified and extracted with dichloromethane. The organic phase was dried, evaporated and the residue recrystallised from 60°–80° petrol to give the title compound (8.8 g) m.p. 52°–4° C.

Found: C, 66.0; H, 6.2; N, 4.4% $C_{17}H_{19}ClFNO$ requires: C, 66.3; H, 6.2; N, 4.6%.

EXAMPLE 6

2-(4-Chlorophenyl)-5-methyl-2,3,4,5-tetrahydro-[6H]-1,5-benzoxazocine

A mixture of 3-(4-chlorophenyl)-N-(2-fluorophenyl)-methyl-3-hydroxy-N-methylpropylamine (3.1 g, 10 mM), prewashed 50% sodium hydride (500 mg, 10 mM) and DMSO (100 ml) was heated for 24 hours at 50° C. The solvent was removed under reduced pressure, the residue partitioned between water and ether and the ether layer dried and evaporated. The residue was chromatographed on Grade 1 silica using 5% methanol in chloroform as eluant, the appropriate fractions combined, evaporated, dissolved in a small volume of IPA and treated with a solution of tosic acid in ether to give the title compound as the tosylate (750 mg), m.p. 186°–7° C.

Found: C, 62.3; H, 5.8; N, 3.1% $C_{17}H_{18}ClNO.C_7H_8SO_3$ requires: C, 62.7; H, 6.0; N, 3.0%.

EXAMPLE 7

N-(2-Fluorophenylmethyl)-3-hydroxy-N-methyl-3-phenylpropylamine

A mixture of N-methyl-o-fluorobenzylamine (27.8 g), 3-chloro-1-phenylpropan-1-ol (34.2 g), 2,2,6,6-tetramethylpiperidine (34.4 ml) and acetonitrile (500 ml) was refluxed for 48 h. The mixture was cooled to room temperature, filtered and the solvent removed. The residue was partitioned between chloroform and aqueous sodium bicarbonate. The organic phase was dried and the solvent removed. The residue was disolved in 60°–80° petrol (150 ml) and allowed to crystallise yielding the title compound (32.4 g) which is cyclodehydrohalogenated as in Example 4.

EXAMPLE 8

5-Ethyl-2-phenyl-2,3,4,5-tetrahydro[6H]-1,5-benzoxazocine

A mixture of 2-phenyl-2,3,4,5-tetrahydro-[6H]-1,5-benzoxazocine (2,39 g, 10 mM), 2,2,6,6-tetramethylpiperidine (1.72 ml, 10 mM), ethyl iodide (0.81 ml, 10 mM) and acetonitrile (100 ml) was stirred 24 h at ambient temperature. The solvent was removed under reduced pressure, the residue partitioned between chloroform and saturated sodium bicarbonate solution and the organic phase dried and the solvent evaporated. The residue was disolved in diisopropyl ether (100 ml), filtered and treated with hydrogen chloride. Removal of the precipitate followed by drying in vacuo gave the title compound as the hydrochloride hemihydrate (1.2 g) m.p. 184°-6° Found: C, 69.6; H, 7.4; N, 4.4%. $C_{18}H_{21}NO.HCl.\frac{1}{2}H_2O$ requires: C, 69.1; H, 7.4; N, 4.5%.

EXAMPLE 9

N-[(5-Chloro-2-fluorophenyl)methyl]-N-methyl-3-hydroxy-3-phenylpropylamine

A mixture of 5-chloro-2-fluorotoluene (2.9 g; prepared by a modified Schiemann reaction on 4-chloro-2-methylaniline), NBS(3.6 g) benzoyl peroxide (100 mg) and carbon tetrachloride (25 ml) was refluxed 2 h. The mixture was cooled, filtered and the solvent removed. Distillation gave 5-chloro-2-fluorobenzyl bromide (3 g), b.p. 104°/15 mm.

A solution of 5-chloro-2-fluorobenzyl bromide (10.5 g) in acetonitrile (100 ml) was added dropwise to a mixture of N-methyl-3-hydroxy-3-phenylpropylamine (7.7 g), 2,2,6,6-tetramethylpiperidine (8 ml) and acetonitrile (100 ml) After 12 h the mixture was filtered, the filtrate evaporated and the residue chromatographed on silica (Woelm Grade 1) using ether as eluant to give the title compound as an oil (10.5 g), b.p. 160°/0.5 mm.

(Found: C, 66.1; H, 6.2; N, 4.1% $C_{17}H_{19}ClFNO$ requires: C, 66.3; H, 6.2; N, 4.55%).

EXAMPLE 10

8-Chloro-5-methyl2-phenyl-2,3,4,5-tetrahydro-[6H]-1,5-benzoxazocine

A mixture of N-(5-chloro-2-fluorophenyl)methyl-N-methyl-3-hydroxy-3-phenylpropylamine (3.1 g), 50% sodium hydride dispersion (480 mg) and DMSO (100 ml) was maintained at 50° under nitrogen for 12 h. The mixture was poured onto water (500 ml) and extracted with ether (3×300 ml) The combined organic extracts were washed, dried and evaporated. Chromatography of the residue on silica (Woelm Grade 1) using ethyl acetate as eluant gave the title compound (1.6 g). This was converted to the tosylate in ether/IPA, m.p. 219°-221°.

(Found: C, 62.2; H, 5.6; N, 2.7%. $C_{17}H_{18}ClNO.C_7H_8SO_3$ requires: C, 62.65; H, 5.7; N, 3.0%).

We claim:

1. A compound of formula (II)

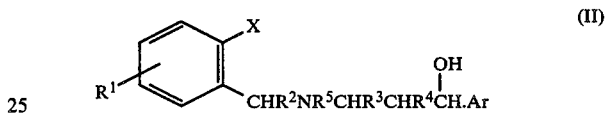

wherein $R^1$ represents hydrogen, or one or more halogen, trifluoromethyl, lower alkyl, lower alkoxy, nitro, $-NH_2$, mono- or di-(lower)alkyl-amino or cyano substituents, $R^2$, $R^3$ and $R^4$, which may be the same or different, each represent hydrogen or lower alkyl or $R^3$ and $R^4$ together represent $-(CH_2)_3-$ or $-(CH_2)_4-$, $R^5$ represents hydrogen, lower alkyl, phenyl(lower)alkyl, cyclobutyl(lower)alkyl or cyclopropyl(lower)alkyl, Ar is a phenyl radical optionally substituted by one or more halogen, trifluoromethyl, lower alkyl, lower alkoxy, nitro or $-NH_2$ groups and X is fluorine, chlorine or bromine.

2. A compound as claimed in claim 1 which is N-(2-fluorophenylmethyl)-3-hydroxy-3-phenylpropylamine.

3. A compound as claimed in claim 1 which is N-(2-fluorophenylmethyl)-3-hydroxy-N-methyl-3-phenylpropylamine.

4. A compound as claimed in claim 1 which is 3-(4-chlorophenyl)-N-(2-fluorophenyl)methyl-3-hydroxy-N-methylpropylamine.

5. A compound as claimed in claim 1 which is N-[(5-chloro-2-fluorophenyl)methyl]-N-methyl-3-hydroxy-3-phenylpropylamine.

* * * * *